United States Patent [19]

Schlogel

[11] Patent Number: 5,195,944
[45] Date of Patent: Mar. 23, 1993

[54] DEVICE FOR ARTICULAR STABILIZATION

[75] Inventor: Gilbert Schlogel, Saint-Tropez, France

[73] Assignees: Societe d'Estudes et de Recherches Creativity, Aix-en-Provence; Cartonnerie Beausoleil, Brignoles, both of France

[21] Appl. No.: 404,183

[22] Filed: Sep. 7, 1989

[30] Foreign Application Priority Data

Sep. 8, 1988 [FR] France ................................ 88 11759

[51] Int. Cl.$^5$ ................................................ A61F 5/04
[52] U.S. Cl. .......................................... 602/5; 602/6; 602/21
[58] Field of Search ............... 128/77, 80 R, 85, 87 R, 128/87 A, 87 C, 94; 602/1, 3, 4, 5, 6, 12, 15, 16, 20, 21, 23, 27, 28

[56] References Cited

U.S. PATENT DOCUMENTS

| 2,409,195 | 10/1946 | Crawford | 128/87 R |
|---|---|---|---|
| 3,624,745 | 11/1971 | Bowers | 128/87 R |
| 3,850,167 | 11/1974 | Seeley | 128/87 R |
| 4,209,011 | 6/1980 | Peck et al. | 128/87 R |
| 4,383,526 | 5/1983 | Robins | 128/87 R |
| 4,520,806 | 6/1985 | Miller | 128/87 R |

FOREIGN PATENT DOCUMENTS 1184459  3/1985  Canada ............................. 128/87 R Primary Examiner—Robert A. Hafer
Assistant Examiner—Sam Rimell
Attorney, Agent, or Firm—Bachman & LaPointe

[57] ABSTRACT

The present invention relates to a device for stabilizing an articulation, such as a splint or a brace. The aim of the invention is to provide such a stabilizing device which is easy to use and manufacture, is disposable and has a very low retail price. These aims are achieved by means of a device for articular stabilization, which comprises a board obtained by means of cutting and having a shape characteristic of the articulation to be protected, this board being made from a thin sheet of deformable material, this board having folding lines for folding the said board by adapting it to the articulation to be protected, means for holding the said board in the folded position and/or means for stabilizing the folded board on the said articulation. This device is more particularly intended to immobilize momentarily an articulation in the event of a fracture.

7 Claims, 4 Drawing Sheets

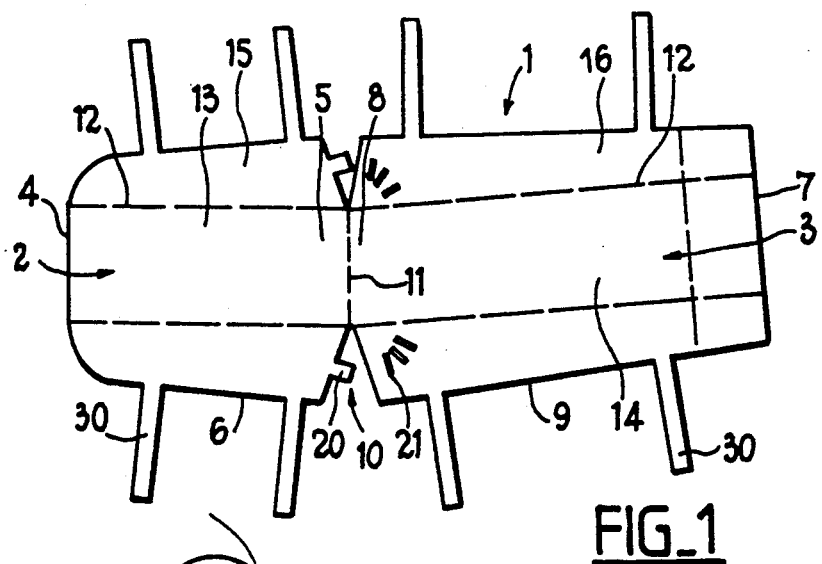
FIG_1
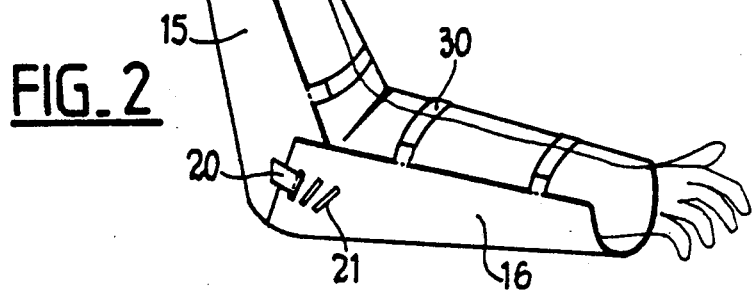
FIG_2
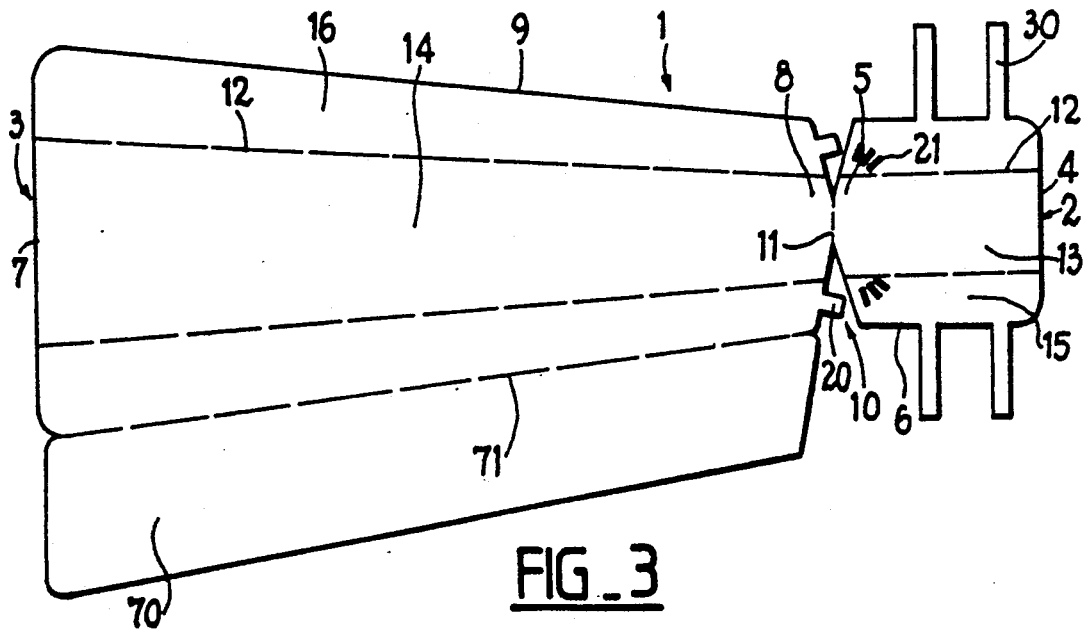
FIG_3

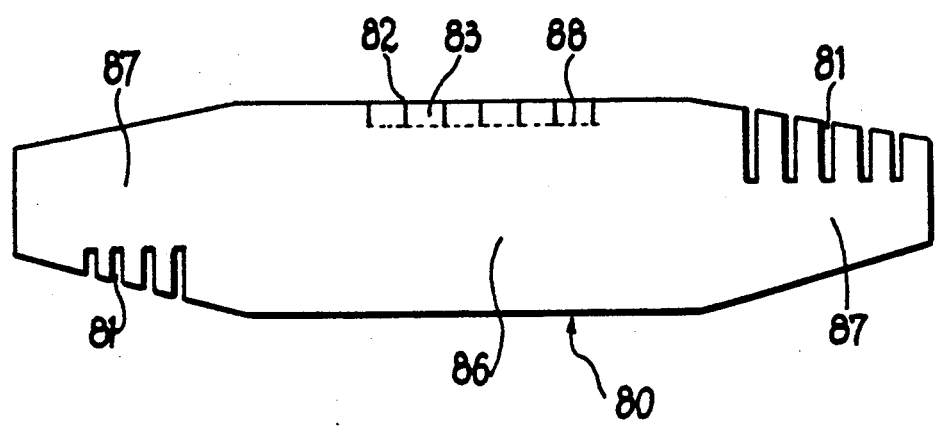
FIG_4
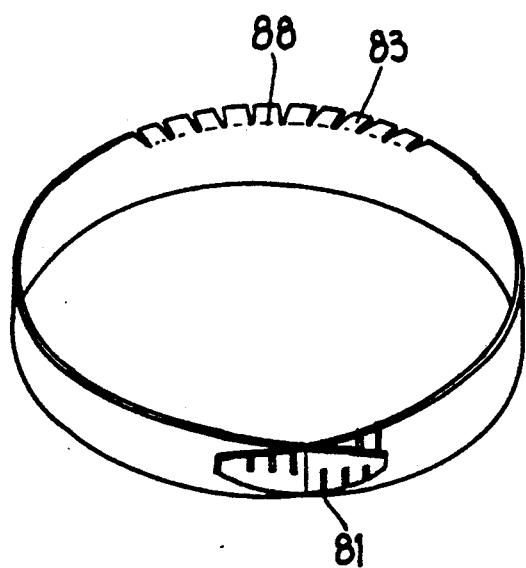
FIG_5

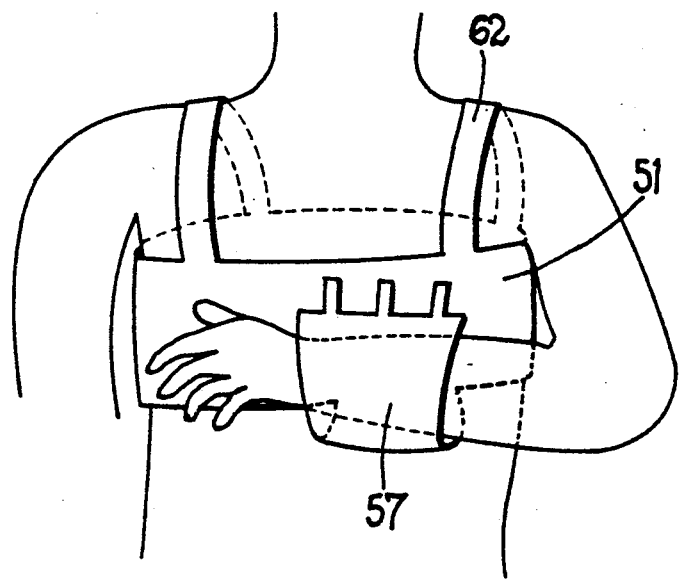
FIG_7
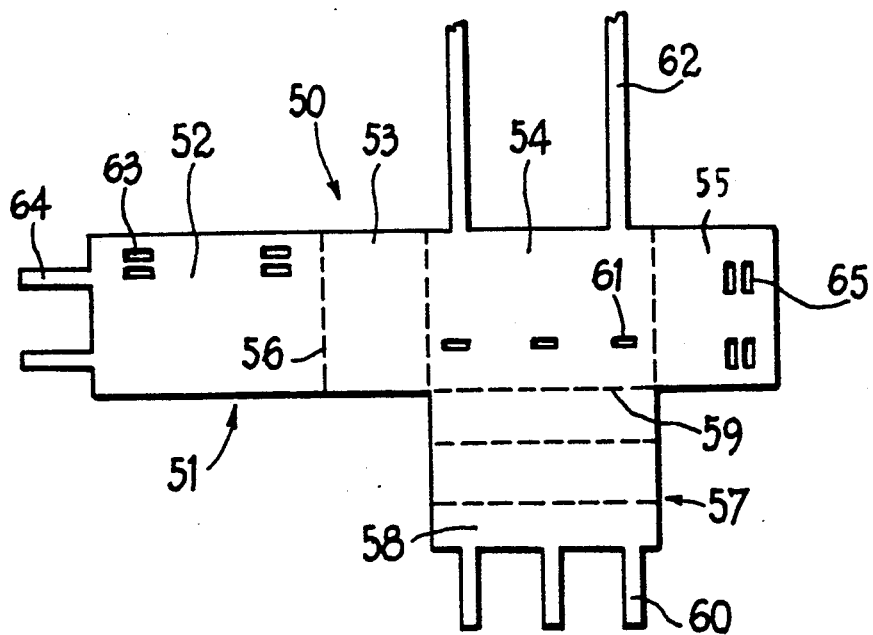
FIG_6

DEVICE FOR ARTICULAR STABILIZATION

The present invention relates to a device for stabilizing an articulation, such as a splint or a brace, and in particular a device intended to be used in an emergency in order to immobilize momentarily an articulation, in the event of a fracture.

When a person breaks an arm or a leg or any other articulation, it is necessary and recommended to immobilize the fractured limb during transportation from the scene of the acident to the hospital or to a doctor's surgery. In fact, if the articulation is not immobilized, the injured person experiences excruciating pain and runs the risk of further complications.

First-aid workers or firemen generally have inflatable splints, which are extremely expensive. These splints are of two types. According to a first variation, they consist of a plastic sleeve which is arranged around the fractured limb and which is then inflated. According to a second variation, they consist of a sleeve filled with small plastic balls, which is arranged around the limb. Then, the residual air contained in the sleeve is sucked out and, the said sleeve, by means of the small balls, assumes the shaped of the contour of the limb and holds the latter in place.

It is often very difficult for firemen or rescue workers to recover a splint when the injured person is rushed to hospital. In fact, to attempt to do so would be dangerous since the fractured limb must not be moved. Owing to the high cost of these splints, this represents a drawback.

For the same reasons, holiday camp centers or schools are reluctant to buy such splints. Moreover, to be able to cope with all the instances of fractures, these centers would have to have splints of different sizes, depending on whether the injured person is a young child, an adolescent or even an adult.

Consequently, in most cases, the injured person is brought to the hospital without a splint, which is extremely damaging for the articulation of the injured person.

Apart from inflatable splints, splints consisting of a wooden board which is held against the limb by means of a bandage are also known. These splints are often prepared in makeshift manner at the scene of the accident and are not very practical.

The aim of the invention is to provide a stabilizing device which is easy to use and manufacture and has a very low retail price.

Another aim of the invention is to provide such a device, which is of the disposable type.

A third aim of the invention is to provide this device in several standardized sizes so as to cover all needs, according to the size of the person injured.

A fourth aim of the invention is to provide this device made of material allowing the circulation of air around the limb and being X-ray transparent, i.e. allowing an X-ray to be taken of the limb without having to remove the splint.

These aims as well as others which will become apparent subsequently are achieved notably by means of a device for articular stabilization, which comprises a flank precut from a thin material, the said flank having, substantially along its axis of symmetry, a longitudinal zone defined by at least two folding lines, this zone being of a width corresponding approximately to that of the part of the body to be immobilized and comprising, on either side of the folding lines, an articulated flange, at least one of the said articulated flanges being extended outwards by a flap forming a cover and tongues and locking slots being provided in the said flanges so as to form by means of overlapping a self-locking peripheral encasement around the said part of the body.

According to another characteristic feature of the invention, the longitudinal zone is divided transversely into two surfaces comprising respectively flanges and flaps provided with locking slots and tongues, these two surfaces being articulated with respect to each other so as to define two orthogonal encasements corresponding to the two parts of the limb to be immobilized, namely the leg and the foot, or the arm and the forearm, respectively, the flanges adjoining each of the two surfaces overlapping in the region of the articulation and self-locking with each other by penetration of the tongues into the corresponding slots.

Other characteristic features and advantages of the invention will become apparent upon reading the description which follows of a preferred embodiment of the invention provided by way of an illustrative example and from the accompanying drawings in which:

FIG. 1 is a plan view of an arm splint according to the invention,

FIG. 2 is an overall view of the splint of FIG. 1 arranged on an arm,

FIG. 3 is a plan view of a leg splint according to the invention,

Figure 8:
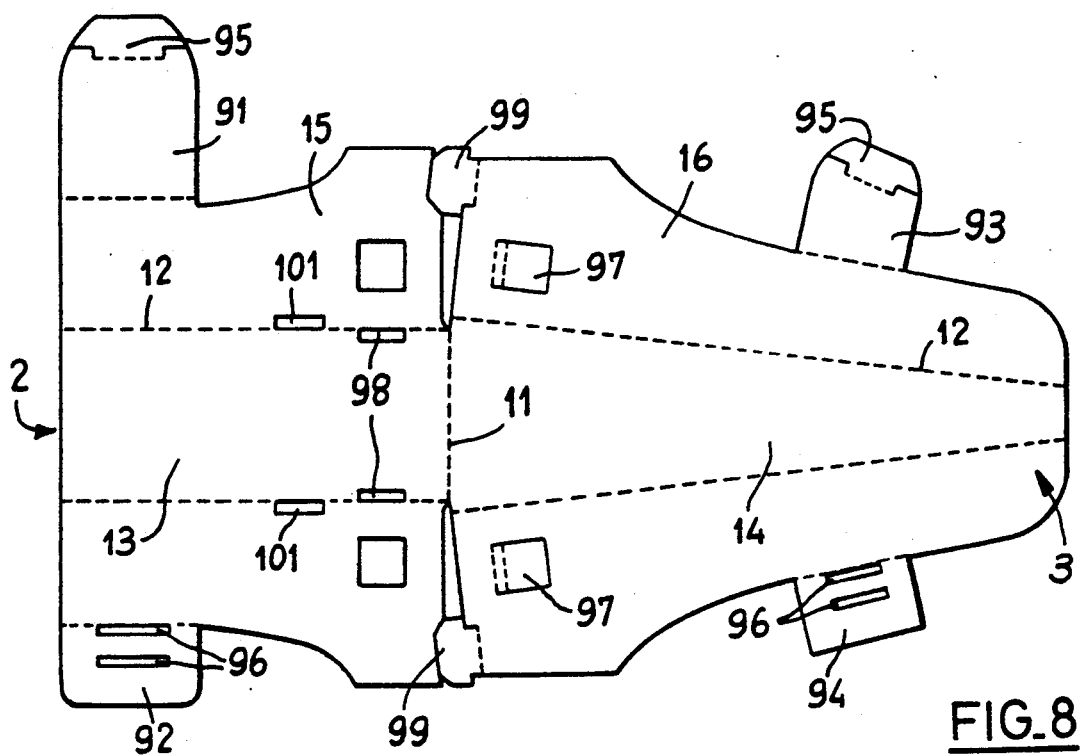
Figure 9:
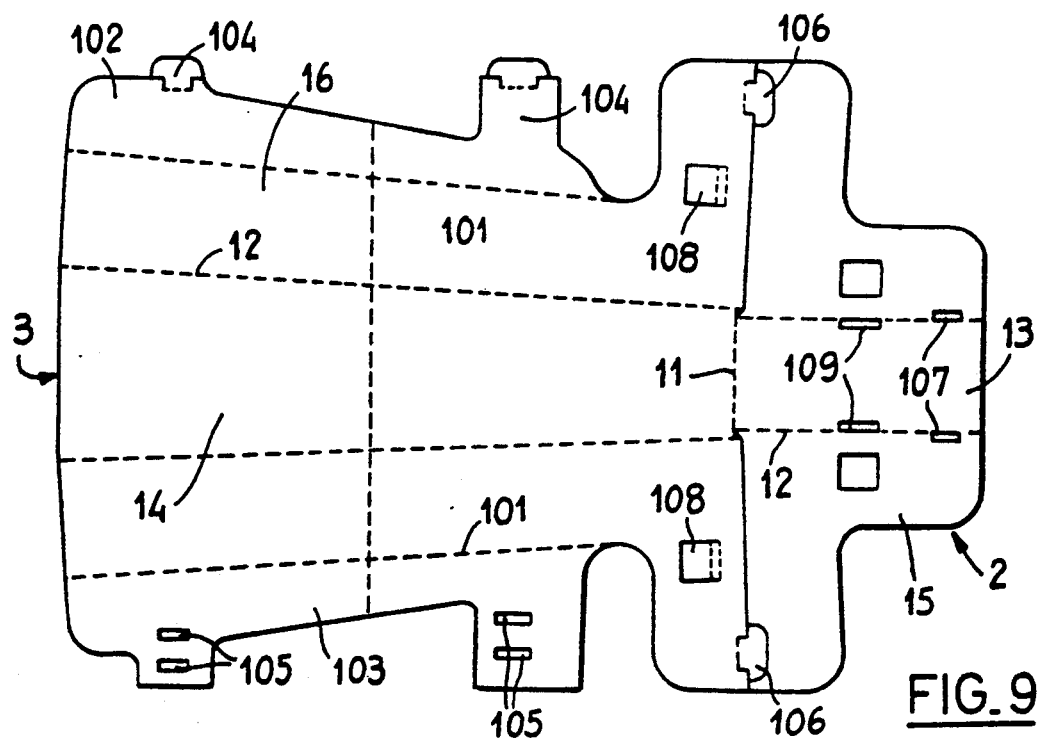

FIG. 4 is a plan view of a brace according to the invention intended to be used for the neck, FIG. 5 is a perspective view of the brace of FIG. 4, FIG. 6 is a plan view of a splint intended to be used for a shoulder fracture, FIG. 7 is an overall view of the splint according to FIG. 6, positioned on an injured person, FIG. 8 is a plan view of another embodiment of an arm splint according to the invention, FIG. 9 is a plan view of another embodiment of a leg splint according to the invention.

The stabilizing devices according to the invention are generally precut from a sheet of thin cardboard, in a shape matching the articulation which is to be immobilized. Nevertheless, they could be cut from any other deformable material which offers protection against humidity or is provided with pores or holes intended to allow the sweat to escape, and which is X-ray transparent. Thus, the limb is prevented from remaining exposed to humidity and becoming infected, in the case of a wound for example. The deformable materials which may be mentioned include corrugated cardboard, plastic or synthetic materials and, possibly, metal sheets or metal meshwork, although the latter do not allow an X-ray to be taken easily.

FIGS. 1, 3, 4 and 6 show, respectively, stabilizing devices intended to protect the joint of the elbow and/or wrist, of the leg and the heel, and of the neck and shoulder. These devices therefore enable more or less all the parts of the body to be stabilized, except for the trunk and the pelvis, as they are made of a material which is too light to support the total weight of the body.

As illustrated in FIG. 1, the stabilizing device consists of a board 1 cut so as to form two integral parts joined by a folding line 11 so as to be articulated with each other. These two parts comprise a shorter part 2, intended to surround the arm, and a longer part 3, intended to surround the forearm and if necessary the wrist. These two parts 2 and 3 have an elongated substantially trapezoidal shape and are joined to each other by their large base. They could also be rectangular.

More precisely, the part for protecting the arm 2 has a small base 4, a large base 5 and two sides 6. The part for protecting the forearm 3 also has a small base 7, a large base 8 and two sides 9. These two parts 2 and 3 are assembled over a part of the length of their respective large bases so as to form two V-shaped cutouts 10 on either side of the said folding line 11.

The two parts 2 and 3 each have moreover, longitudinally, two parallel folding lines 12. These folding lines 12 divide substantially into three the width of each of the parts 2 and 3 and thus define in the center a bottom 13 for the part 2, a bottom 14 for the part 3, two lateral shoulders 15 for the part 2 and two lateral shoulders 16 for the part 3. It is important that the end of the folding lines 12 should intersect the end of the folding line 11 and the V-shaped part of the recess 10, precisely so as to allow easy folding.

When the shoulders 15 and 16 are folded along the folding lines 12, they form with the bottom 13 bottoms 13 and 14 a sleeve surrounding the arm and the forearm. Moreover, the two parts 2 and 3 articulated along the folding line 11 are moved towards each other so as to form an angle varying between 135° and 60°, depending on whether it is required to place this splint on an articulation which is flexed to a greater or lesser extent. In order to keep the various folded parts in position and in particular maintain the angle of inclination between the two parts 2 and 3, various holding means are envisaged.

According to a first variation and embodiment, these holding means may consist of two tongues 20 each arranged in the region of the V-shaped cutout 10 along the large base 5 of the part 2 and capable of being introduced into slits 21 provided for this purpose in each shoulder 16 of the part 3. Vice versa, the slits 21 may be provided in the shoulders 16 and the tongues 20 on the shoulders 16.

More precisely, each tongue 20 forms a block with the shoulder 15 and extends substantially perpendicularly in the center of one of the sides of the V-shaped cutout 10. Preferably three slits 21 are provided in each shoulder 16, but this number is not restrictive. These slits 21 are arranged in the vicinity of the V-shaped cutout 10 and are thus located opposite the tongues 20. These slits 20 are arranged along the radii of an imaginary circle, the center of which is situated at the tip of the V of the cutout 10. Thus, the further from the edge of the cutout 10 the tongue 20 is inserted into a slit 21, the more acute the angle between the two parts 2 and 3.

According to a second variation and embodiment of the means for holding the board in a folded position, the tongues 20 can be retained and the slits 21 eliminated. In this case, adhesive films provided with a peel-off protective sheet are arranged on the lower or upper face of the tongues 20. In order to maintain the angle of inclination between the parts 2 and 3, it is sufficient to affix the tongues 20 onto the shoulders 16 on the inside or outside of the latter.

According to a third variation and embodiment (see FIG. 2), it is possible to retain the slits 21 and provide the tongues 20 with adhesives so that the said tongues can be passed into the said slits 21 from the inside towards the outside and then, after folding the tongues, affixed onto the outer side of the sleeve, and vice versa.

According to a fourth variation, it is possible to replace the tongue/slit system with self-gripping strips known commercially under the name "velcro".

Generally, use will be made of any fixing system enabling the inclination to be maintained between the two parts, and for example, bonding or fastening.

The system enabling variation of the angle of inclination between the part protecting the arm 2 and the part protecting the forearm 3 is very useful since, in the case of accidents, the arm may be in any position and it must be immobilized in this position, without moving the arm, otherwise the injured person will be made to suffer unnecessarily.

As illustrated in FIG. 3, it is possible to adapt the device for stabilizing the elbow joint to the the heel joint. In this case, the small part 2' serves to protect the foot and the long part 3' serves to protect the leg and the thigh; this part is consequently long enough to surround the entire length of the lower limb. Since this splint, apart from these dimensions, is substantially identical to the one described above with respect to FIGS. 1 and 2, similar references will be retained for identical parts. Thus, board 1' includes bases 4' and 5' of part 2' and sides 6' of part 2', bases 7' and 8' of part 3' and sides 9' of part 3'. The V-shaped cut-outs 10' are provided similar to cut-outs 10 in FIGS. 1 and 2. Folding lines 12' form bottom 13' for part 2' and bottom 14' for part 3'.

When the board 1' has been folded along the folding lines 11' and 12' and the tongues 20' have been introduced into the corresponding slits 21' so as to form the protection sleeve, the articulation is placed inside this folded board. It is then necessary to stabilize this board on the articulation. For this purpose, according to the first embodiment shown in FIGS. 1 and 2, use is made of ties 30 making it possible to close the sleeve which surrounds only three sides of the arm. These ties may be separate from the sleeve and simply tied around the latter. They may consist of thin cords, strips of paper, fabric or plastic, or elastic bands, similar ties 30' are shown in FIG. 3.

These ties 30 may also be formed so as to be integral with the board 1, in which case they are made of the same material as the latter and are obtained by means of cutting.

Preferably, during manufacture and precutting of the board 1, provision is made for two ties on each shoulder 15 and 16, i.e. eight ties in total as shown in FIGS. 1 and 2. These ties extend substantially perpendicularly to the axis of the folding lines 12 and consist of narrow, substantially rectangular strips.

According to another variation and embodiment, the means for stabilizing the folded board on the articulation may consist of a cover 70 (see FIG. 3). In this case, provision is made, during cutting along one of the shoulders 15', for a substantially rectangular strip with dimensions similar to that of the bottom 14'. This strip forming the cover 70 is articulated with respect to the shoulder 15' or 16' by means of a folding line 71. This cover forms the fourth part of the sleeve and is folded down onto the opening of the latter. This cover is kept in position by fixing means such as tongues cooperating with slits, adhesive films with peel-off protective film, self-gripping strips or slots cooperating with each other.

According to a variation, this cover 70 may be completely separate and fixed on each side to the shoulders 15' or 16' by the various fixing means mentioned above.

The splints described above related to the articulation of the elbow and of the heel, but it is of course possible to adopt the same principle for other articulations, retaining the same materials and identical folding and fixing means.

Thus, FIG. 6 illustrates a board 50 precut so as to form a splint for the shoulder articulation. In fact, in the event of fracture of the shoulder or arm, it is necessary to keep the arm close up against the torso, vertically.

The board 50 comprises an elongated rectangular band 51 surrounding the torso. This band 51 is divided into two parts substantially in the middle of its length. Each of these two parts is divided in turn into two parts of unequal length.

The band 51 therefore consists of a part 52, placed against the back of the patient (on the left in the drawing), a right-hand side piece 53, placed along the right-hand side of the patient, a front piece 54, intended to be placed in front of the chest, and a left-hand side piece 55 placed along the left-hand side of the patient.

The two side pieces 53 and 55 are of the same length. The back piece 52 and the front piece 54, identical in length, are substantially twice the length of the side pieces 53 and 55.

The demarcations between the four parts are made by means of three folding lines 56.

The front piece 54 has, at its base, a rectangular extension 57 constituting the support for the forearm. This forearm support 57 is the same length as the front piece 54 and of sufficient height to surround the forearm. It has substantially, in the middle of its height, two folding lines 58 extending parallel to the longitudinal axis of the band 51. Moreover, the forearm support 57 is articulated with respect to the band 51 by a folding line 59.

The forearm support 57 has, at the bottom, three fixing tongues 60 distributed uniformly over its entire length and intended to be placed in slits 61 provided for this purpose in the front piece 54. The front piece 54 has moreover, at the top, two straps 62 designed to hold the band 51 around the body, the said straps being passed over the shoulders of the patient and these straps being fastened inside slits 63 provided for this purpose at the top of the back piece 52. The free side end of the back piece 52 (on the left in the drawing) is provided with two fixing tongues 64 designed to engage into two slits 65 provided for this purpose in the left-hand side piece 55. The tongues 64 and the slits 65 are located opposite each other symmetrically relative to the middle axis of the band 51.

As illustrated in FIG. 7, the folding lines 56, 58 and 59 are folded so as to form a shell surrounding the trunk of the patient and a sleeve surrounding the forearm. The part of the extension 57 provided with tongues 60 forms a cover for the said sleeve and enables the latter to be stabilized on the arm.

The above description relating to the shoulder splint is only a preferred embodiment, but as for the elbow or leg splint, the fixing means could be replaced by slits and tongues, by fixing means which are adhesive or have self-gripping strips (marketed under the name "Velcro"), or fasteners. Furthermore, even in the embodiment with slits or tongues, it is possible to place several slits 61, 63, 65 in parallel, instead of a single one, so as to have several possibilities for adjustment.

FIGS. 4 and 5 illustrate a splint for the neck, designed on the same principle as the preceding ones.

This splint consists of a board 80 of substantially rectangular elongate shape. This board 80 has a wider central part 86 and two ends 87 which taper uniformly and have a substantially trapezoidal shape. One of the edges of the central part 86 has several fine slits 82 of limited depth defining between them small tongues 83. The edge of the board 80 with the tongues 83 will be called the upper edge since, when the splint is in place, this edge will be located at the top, underneath the patient's jaw.

Provision is made, moreover, at one of the ends 87, for slots 81 cut perpendicularly to the upper edge and, at the other end, for identical slots 81 cut in the lower chamfered edge. The two series of slots 81 are parallel with each other and fairly deep.

When the neck of the patient is surrounded with the splint 80, the latter is arranged as illustrated in FIG. 5, i.e. the two ends 87 of the board 80 are crossed so as to bring the slots 81 of one of the ends opposite the slots 81 of the other end and thus fix the splint in the desired position. The tongues 83 are then folded outwards, along a folding line 88, so as to support the lower jaw when the splint is in place.

As above, the slots 81 could be replaced by any other type of fixing means.

Preferably, this splint will be made of corrugated cardboard, the longitudinal axis of the undulations being located perpendicularly to the longitudinal axis of the board 80. Thus, the board 80 may be easily wound around the neck of the patient. It is, on the other hand, very difficult to fold the splint in the other direction and thus the patient cannot move his or her head downwards since the jaw is firmly held.

FIG. 8 shows a variation and embodiment of FIG. 1 of an arm splint according to the present invention. In this figure the elements corresponding to those of FIG. 1 have been denoted by similar reference numbers. The part protecting the arm 2' and the part protecting the forearm 3', the folding lines 11' and 12', the bottoms 13' and 14' and the lateral shoulders 15' and 16' are thus shown again as in FIG. 1.

In this embodiment, locking is obtained by means of strips of considerable thickness which are arranged on the outer edges of the shoulders or flanges 15' and 16', being integral with the latter. When the splint is in the working position, these wide strips form a partial cover element which protects the limb. In the embodiment shown, the part protecting the arm 2' and the part protecting the forearm 3' each have two strips 91 and 92, and 93 and 94, respectively, which form half-covers fitting one inside the other; for this purpose, one of the two strips, the strips 91 and 93 in the example shown, has a tongue 95 which is able to engage into slots 96 provided in the other strip, i.e. the strips 92 and 94.

Locking of the splint in the working position is also obtained by means of a tongue 97 provided in the shoulder 16' and cooperating with a slot 98 provided along the folding line 12' of the part 2'. Provision is also made for a tongue 99 arranged on the outer part of the shoulder 16' and projecting from the latter; this tongue 99 cooperates with a slot 101 provided also in the part 2' along the folding line 12'.

FIG. 9 shows a variation of embodiment of a leg splint which has two elements forming a half-cover and making up a complete cover protecting the whole of the limb. In this figure, the element corresponding to those of FIG. 3 have been denoted by similar reference numbers.

In this embodiment, provision has been made, in the part 3', for two additional folding lines 101 which are substantially parallel to the folding lines 12' and which delimit two outer elements 102 and 103 forming half-covers which make up, when the leg is in the working position, a complete cover so as to surround entirely the protected limb.

The locking devices consist of tongues 104 projecting outside the half-cover 102 and cooperating with slits 105 provided in the half-cover 103. Furthermore, provision has been made in the shoulder 16' of the part 3' for a projecting tongue 106 which cooperates with a slot 107 provided along the folding line 12' of the part 2'; another tongue 108 cut in the shoulder 16' and articulated on the latter is also fixed inside a slot 109 provided along the folding line 12' of the part 3'.

Of course, the invention is not limited to the example of embodiment described above, in place of which other variations of embodiment may be envisaged without thereby departing from the scope of the invention.

I claim:

1. A device for articular stabilization of a part of the body which comprises:

a sheet of thin material having a central portion extending longitudinally and having a width corresponding approximately to that of the part of the body to be stabilized wherein said central portion has longitudinal sides;

articulated flanges connected to the longitudinal sides of the central portion, said longitudinal sides of the central portion defining at least two folding lines;

stabilization means extending outwards from at least one of said articulated flanges and forming a continuous cover around a substantial portion of said part of the body; and holding means cooperating with said stabilization means for holding said articulated flanges in a closed position so as to form a peripheral encasement around said part of the body and for defining angular locking means, said holding means comprising planar tongues and locking slots, said planar tongues and said locking slots both being provided in said flanges, said tongues extending outwards from said flanges and being designed to enter into said locking slots provided in a flange opposite to the flange having the tongues to lock the articulated flanges in place;

wherein said articulated flanges, said stabilization means and said holding means form an integral part of said sheet of thin material so as to form a one piece device.

2. A device according to claim 1 wherein the central portion is divided transversely into two surfaces and wherein said articulated flanges include all of said holding means, said two surfaces being articulated with respect to each other, and wherein each of said surfaces includes at least two articulated flanges.

3. A device according to claim 2 wherein each of said surfaces includes said stabilization means and holding means and defines two substantially orthogonal peripheral encasements, and wherein said articulated flanges of the two surfaces overlap in the region of the articulation and said stabilization means includes at least two overlapping members for forming said cover.

4. A device according to claim 3 wherein said angular locking means comprise tongues extending outwards from one of said surfaces and slots provided in the other surface.

5. A device according to claim 4 wherein a plurality of spaced apart slots are formed in a flange for receiving a tongue, said spaced apart slots being aligned substantially perpendicular to the longitudinal direction of the central portion.

6. A device according to claim 1 formed solely from cardboard material.

7. A device according to claim 3 wherein said two surfaces define two V-shaped cutouts adjacent said transverse division and adjacent said articulated flanges so that said tongues extend into said V-shaped cutouts.

* * * * *